(12) United States Patent
Dees et al.

(10) Patent No.: US 6,541,223 B2
(45) Date of Patent: Apr. 1, 2003

(54) METHOD FOR ENHANCED PROTEIN STABILIZATION AND FOR PRODUCTION OF CELL LINES USEFUL FOR PRODUCTION OF SUCH STABILIZED PROTEINS

(75) Inventors: H. Craig Dees, Knoxville, TN (US); John Smolik, Loudon, TN (US)

(73) Assignee: Photogen, Inc., Knoxville, TN (US)

( * ) Notice: Subject to any disclaimer, the term of this patent is extended or adjusted under 35 U.S.C. 154(b) by 0 days.

(21) Appl. No.: 09/803,609

(22) Filed: Mar. 9, 2001

(65) Prior Publication Data

US 2001/0044146 A1 Nov. 22, 2001

Related U.S. Application Data

(62) Division of application No. 09/543,479, filed on Sep. 6, 2000.
(60) Provisional application No. 60/136,676, filed on May 28, 1999.

(51) Int. Cl.[7] .............................. C12N 5/06; C12N 5/16; C12N 5/08

(52) U.S. Cl. .......................... 435/69.1; 435/325; 435/6; 435/366; 435/367; 435/235.1; 435/339

(58) Field of Search ............................ 435/325, 6, 339, 435/366, 367, 375, 69.1, 69.3, 235.1

(56) References Cited

U.S. PATENT DOCUMENTS

| | | |
|---|---|---|
| 5,188,964 A | 2/1993 | McGuire et al. |
| 5,302,518 A | 4/1994 | Neupert et al. |
| 5,347,945 A | 9/1994 | Berberian et al. |
| 5,447,843 A | 9/1995 | McGuire et al. |
| 5,474,892 A | 12/1995 | Jakob et al. |
| 5,652,115 A | 7/1997 | Marks et al. |
| 5,750,119 A | 5/1998 | Srivastava |
| 5,827,712 A | 10/1998 | Yokoyama et al. |
| 5,830,464 A | 11/1998 | Srivastava |
| 5,837,251 A | 11/1998 | Srivastava |

OTHER PUBLICATIONS

Duprex et al., In vitro and in vivo infection of neural cells by a recombinant measles virus expressing enhanced green fluorescent protein, 2000, Journal of Virology, pp. 7972–7979.*

Ofir et al., Tyrosine phosphorylation of measles virus P–phosphoprotein in persistently infected neuroblastoma cells, 1996, Virus Genes, vol. 13, pp. 203–210.*

D.Y. Vasconcelos et al. Constitutive overpression of the major inducible 70 kDa heat shock protein mediates large plaque foemation by measles virus Journal of General Virology 1998 79. 2239–2247.*

Transfection of the human heme oxygenase gene into rabbit coronary microvessel endothelial cells: Protective effect against heme and hemoglobin toxicity vol. 92 pp. 6798–6802 Jul. 1995.*

Vasconcelos et al. The cellular stress response increase measles viru–induced cytopathic effect Journal of General Virology 1998 79. 1769–1773.*

Kramer et al. Chinese hamster ovary cells are non–permissive towards infection with coxsackievirus B3 despite functional virus–receptor interactions Virus Research 48 1997 149,156.*

Qing et al. Human fibroblast growth factor receptor 1 is a co–receptor for infection by adeno–associated virus 2 Nature Medicine vol. 5 No. 1 Jan. 1999.*

"Human Hsp70 and Hsp40 Chaperone Proteins Facilitate Human Papillomavirus–11 E1 Protein Binding to the Origin and Stimulate Cell–free DNA Replication" The Journal of Biological Chemistry, vol. 273 No. 46, pp. 30704–30712—1998.

"Constitutive overexpression of the major inducible 70 kDa heat shock protein mediates large plaque formation by measles virus" Journal of General Virology, vol. 79, pp. 2239–2247—1998.

"The cellular stress response increases measles virus–induced cytopathic effect" Journal of General Virology, vol. 79, pp. 1769–1773—1998.

"Human Heat Shock Protein 70 (hsp70) Protects Murine Cells from Injury during Metabolic Stress" The American Scoiety for Clinincal Investigation, Inc., vol. 92, pp. 503–508—Jul. 1993.

"Correlation between the Induction of Heat Shock Protein 70 and Enhanced Viral Reactivation in Mammalian Cells Treated with Ultraviolet Light and Heat Shock" Cancer Research, vol. 49 pp. 2735–2742—May 15, 1989.

(List continued on next page.)

Primary Examiner—James Ketter
Assistant Examiner—Konstantina Katcheves
(74) Attorney, Agent, or Firm—Cook, Alex, McFarron, Manzo, Cummings & Mehler, Ltd.

(57) ABSTRACT

A method for increasing production yield of viruses, viral proteins, and other related biological materials through enhanced control and stabilization of protein production via stress proteins and the resultant protein products. The present invention is also directed to methods for selection or engineering of cell lines yielding such enhanced stabilized products. More specifically, example embodiments of the present invention are directed to methods for enhancing production of a viral agent, production of cell lines exhibiting permanent genetic modification, production of permissive eucaryotic cell lines, enhancing functional recombinant product yield, and the products of such methods.

8 Claims, 5 Drawing Sheets

OTHER PUBLICATIONS

"Heat-shock-induced enhanced reactivation of UV-irradiated Herpesvirus" Mutation Research, vol. 146, pp. 121–128—1985.

"The highly inducible member of the 70 kDa family of heat shock proteins increases canine distemper virus polymerase activity" Journal of General Virology, vol. 77, pp. 2125–2135—1996.

"Enhanced Measles Virus cDNA Rescue and Gene Expression after Heat Shock" Journal of Virology, vol. 73, No. 5, pp. 3560–3566—May 1999.

Griffin, Diane E. and William J. Bellini, "Measles Virus", Fields Virology, 1996, (3rd edition), Chapter 43.

Roizman, Bernard and Peter Palese, "Multiplication of Viruses: An Overview", Fields Virology, 1996 (3rd edition), Chapter 4.

* cited by examiner

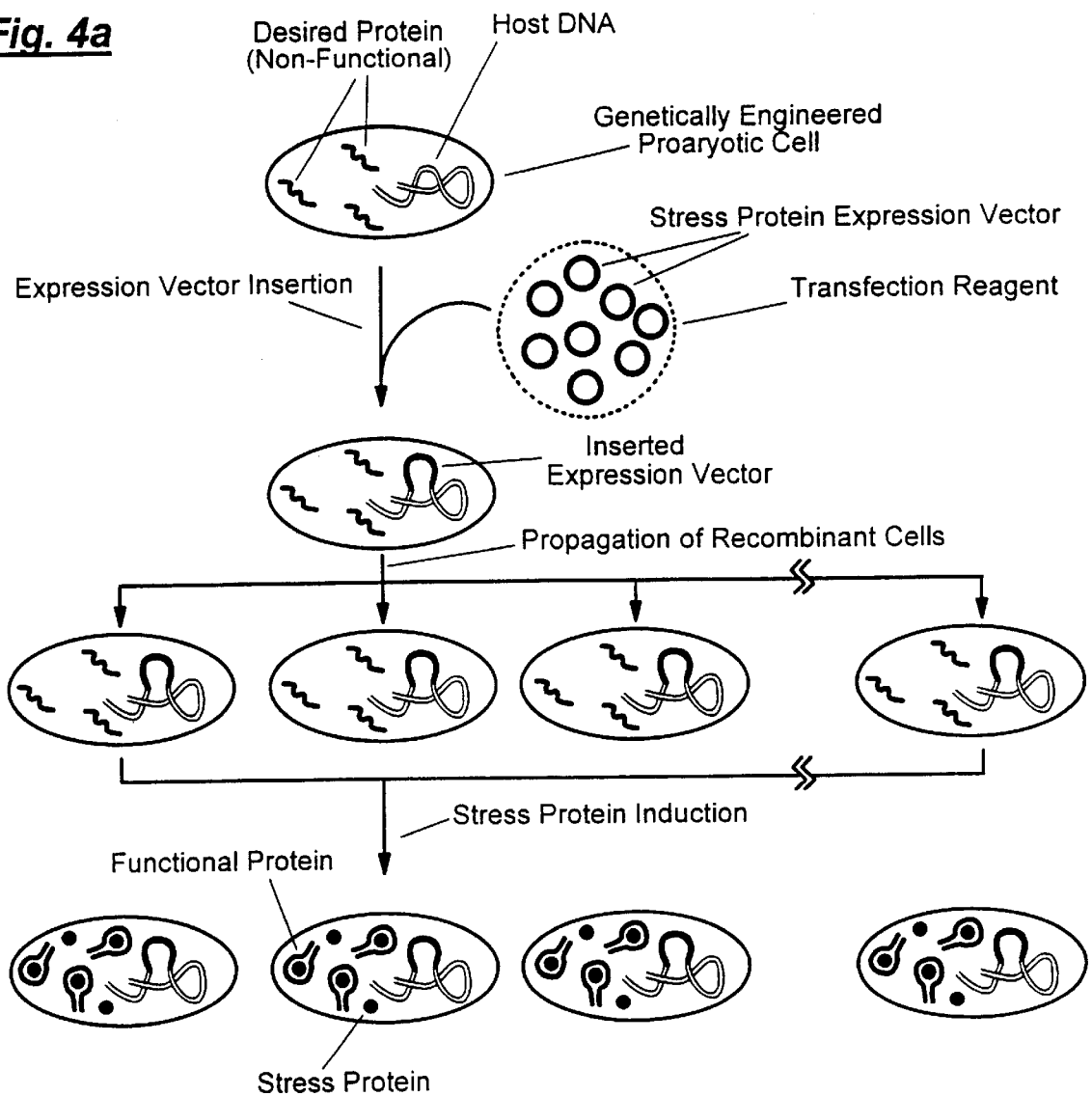

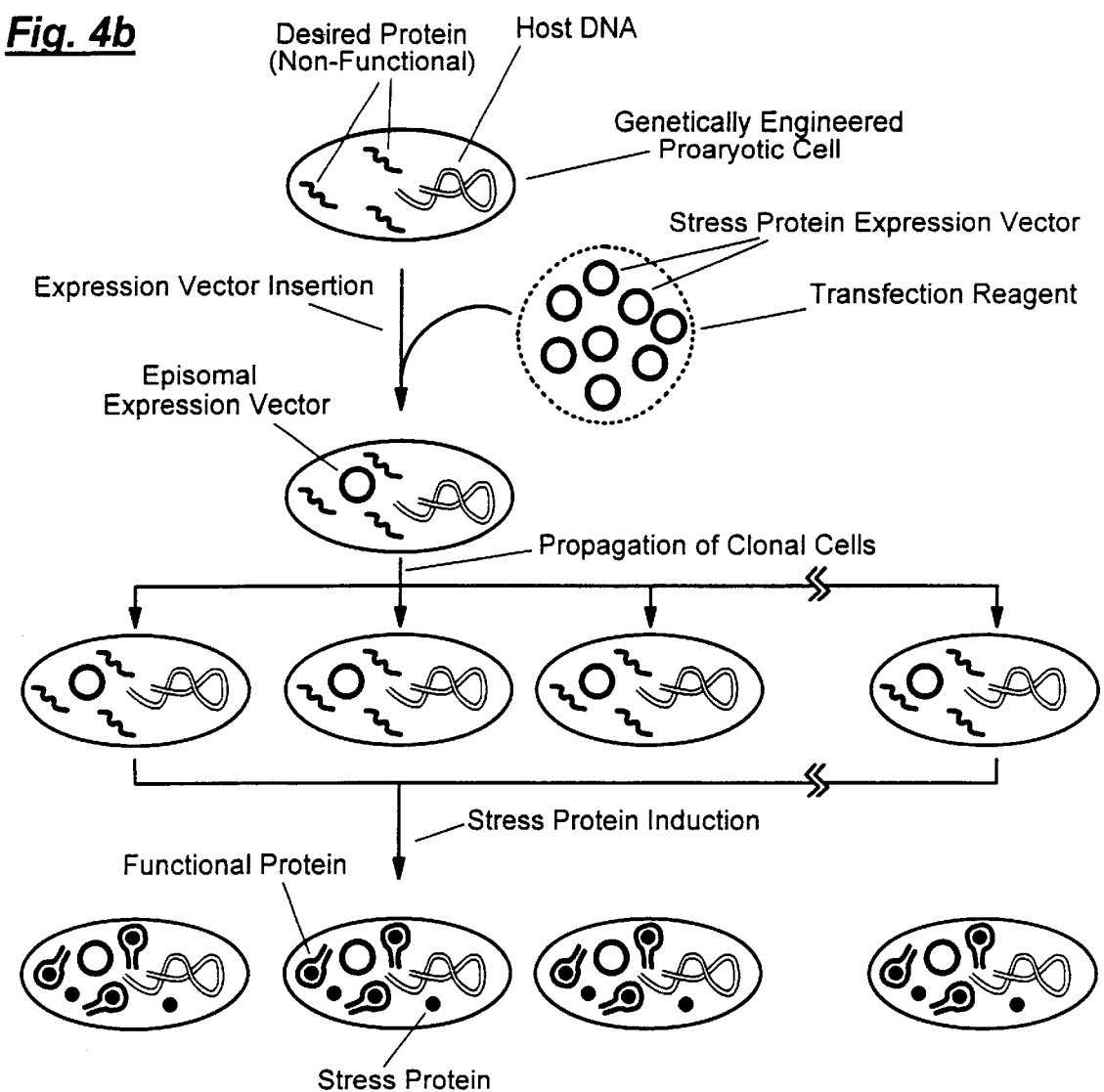

METHOD FOR ENHANCED PROTEIN STABILIZATION AND FOR PRODUCTION OF CELL LINES USEFUL FOR PRODUCTION OF SUCH STABILIZED PROTEINS

This application is a divisional of co-pending application Ser. No. 09/543,479 filed Apr. 6, 2000.

BACKGROUND OF THE INVENTION

This application claims benefit of now abandoned U.S. provisional application Serial No. 60/136,676 filed on May 28, 1999 for the same inventors.

The present invention relates to the production and stabilization of functional biological materials, such as proteins, viral agents, or other biological agents or products, including, but not limited to, enzymes, hormones, growth factors, structural proteins, tumor suppressor agents, nucleic acids and nucleic acid probes, vaccines, antigens, antibiotics, lipids, simple and complex carbohydrates, alcohols and other solvents and the products of those methods. Such functional biological materials are useful for the manufacture of vaccines and diagnostic assays or tests, for example.

The production of viruses, viral antigens, and other viral products useful for manufacturing of products such as vaccines and diagnostic assays, however, is expensive, time consuming and requires a high level of technical expertise. Viruses must be propagated in living eucaryotic cells. Eucaryotic cells that can be infected with a particular virus are said to be "permissive" for that virus. However, most eucaryotic cells are not permissive for any given virus, and no techniques exist to predict permissiveness. Additionally, cells that are permissive for virus production may have different levels of permissiveness. Some cell lines may produce large amounts of virus while others may permit only a low level of viral replication. Therefore, to determine the optimal cells for virus production, a sometimes large and often time-consuming empirical study of many cell lines must be performed. Further complicating matters, the optimal cell line may not be from the host (e.g., human cells for viruses affecting humans) from which the virus was obtained. Frequently, no suitable cell line exists for a virus from a particular host.

Cell lines are preferable to primary cell cultures from a host because of their stability, immortality, known characteristics, and behavior that has been defined by long experience. The requirements for use of such cell lines in viral production has led to development of a large number of exotic cell lines that are used to produce various viruses. For example, Canine Distemper Virus (CDV), a morbillivirus, grows well in Vero cells (i.e. African Green Monkey kidney cells) but is not propagated in cells from dogs, while Bovine Leukemia Virus (BLV) is produced from a cell line derived from bat lung tissue.

Unfortunately, growth of viruses in cell lines far removed from the host and tissue normally infected may cause such viruses to act in a fashion that is far removed from their normal behavior.

Further, the complex pathology for the virus can make the manufacture of viruses extremely difficult. For example, CDV and Human Measles Virus (HMV) are closely related viruses. Both viruses act similarly when infecting their respective canine and human hosts. Both produce encephalitis and long-term sequelae in which the central nervous system is damaged or destroyed. The central nervous system disease in dogs that occurs many years after initial CDV infection is called old dog encephalitis (ODE). In humans, the corresponding condition is subacute sclerosing panencephalitis (SSPE). The cause of ODE and SSPE is directly related to the number of virions produced and cells affected during the encephalitic phase of the disease. This in turn is directly related to permissiveness of the brain cells and the ability of the host's immune system to rapidly respond to the virus. Dogs or humans whose brain viral titers reach exceptionally high levels may develop these long-term consequences many years later. In fact, the high viral titers in some infected patients can result in permanent production of a viral protein in brain cells, even after the infection has cleared. The immune system recognizes the viral protein as foreign and continues to attack it even though no viable virus has been produced for many years. Eventually the combat between the host's immune system and these aberrant cells creates enough damage to destroy the host's cognitive capacity. Dogs with ODE are usually euthanized. The outcome of SSPE in humans is a progressive dementia eventually followed by death. Because of this complex disease pathophysiology, use of manufactured viruses and viral products has been unsuccessful in stimulating immunity in vivo.

Since many viruses (such as CDV and HMV) infect brain cells, the permissiveness of brain cell lines is important in studying the pathophysiology of the resultant disease and in producing viruses for diagnostics and vaccines that exactly mimic virus characteristics during natural infection. However, few neural cell lines exist, and they only produce low levels of CDV or HMV. Therefore, these cell lines produce inadequate levels of the virus for study and are especially unsuitable for antigen or vaccine production. A method of modifying such cells or cell lines, and the cell lines themselves, is thus required that will support replication of viruses and viral products to high levels.

In addition to the problems associated with producing known viruses to useful titers, it is extremely difficult to search for an unknown virus because the cell type required for replication of the unknown virus is itself unknown. For example, there are a number of diseases of the central nervous system that may well be caused by undiscovered viral agents. The degenerative diseases of Creutzfield-Jacob Disease (CJD, affecting humans), scrapie (affecting sheep), and bovine spongiform encephalopathy (affecting cattle) all are very slow neurodegenerative diseases whose etiology remains unknown. To date, no causative agent for these diseases has been identified nor has any viral agent been propagated from infected human or animal brain tissue. This has lead to the promotion of various unorthodox hypotheses concerning disease etiology, including suggestions that a special protein (called a "prion", suggested to be an agent capable of causing infection and reproducing without any genetic material) might serve as the infectious agent. However, no cell line that produces prions, even to high levels, has been shown to be infectious. Transgenic mice modified to produce prions are not infectious even when they present the diagnostic hallmarks of the disease. Thus, without means for identification of the infectious agent, no good diagnostic test can be produced for these diseases, and the production of a vaccine is impossible.

Recently, the need for improved ways for development of diagnostic tests and potential vaccines has become of pressing importance. For example, recently cattle in Great Britain were fed meal consisting of sheep and other animal offal. Bovine spongiform encephalopathy was subsequently recognized for the first time in these cattle. A number of humans were infected by eating meat from the infected cattle—constituting a route of infection which had not been previously recognized (now called "new variant CJD", or nvCJD). Besides the tragic consequences to the infected humans, the slaughter of cattle caused massive economic damage. The finding of nvCJD also produced political repercussions involving the import, export and sale of food and other animal products that might come from infected cattle. Accordingly, the development of a good diagnostic test is required along with the production of an efficacious vaccine. To accomplish these and similar goals, permissive cell lines are required that will allow the propagation of neutrotrophic agents responsible for the etiology of slow dementias like CJD and nvCJD.

As the average age of a nation's population increases, the incidence of disease states like Alzheimer's also increases. Alzheimer's disease is a slowly progressing dementia necessitating difficult, long-term care for the patient. Costs associated with such long-term debilitating diseases can be devastating. Alzheimer's is not thought to be infectious. However, certain features of Alzheimer's have caused speculation that infection with an unconventional viral agent (similar to nvCJD) might cause the disease. It may also be possible that a neurotrophic agent, like HMV or related morbillivirus-like viruses, cause the slow disease process that destroys mentation. If Alzheimer's were caused by an infectious agents, this would have huge consequences for the management, prevention, diagnosis and cure (if possible) of the disease. Then, for example, prevention of Alzheimer's would likely require the development of a good vaccine. However, as is the case with other dementias produced by unconventional agents (such as ODE and SSPE), no definitive diagnostic test exists. Isolation of a virus from infected brain tissue would thus be a landmark step in diagnosing and possibly treating humans with this disease. Hence, cell lines that are more permissive for viruses like measles may allow the isolation of neurotrophic agents (like CDV and HMV) not yet discovered.

Production of proteins from eucaryotic cell lines using recombinant DNA technologies for vaccines, diagnostic kits or other purposes has the same limitations and problems associated with virus production. Recombinant proteins must be produced by eucaryotic cell lines to assure proper folding, glycosylation, and other constitutive factors that are critical to proper function and stability of the protein or its immunogenicity as a diagnostic reagent or vaccine. The ability to produce these proteins in large quantity while maintaining the correct conformation is difficult. In many cases, a recombinant protein may be produced in cell lines at acceptable levels, but due to some often subtle change in conformation, it is either non-immunoreactive as a diagnostic antigen or vaccine or fails to perform its desired function. For example, Canine Parvo Virus (CPV) was genetically cloned and produced in a eucaryotic cell line at levels which would be commercially feasible. Dogs vaccinated with these recombinant antigens responded by producing antibodies that could, in vitro, neutralize infectious (wild type) parvovirus. Unfortunately, all dogs vaccinated with the recombinant antigen died upon exposure to infectious CPV. It is likely that some slight conformation change prevented the recombinant vaccine from protecting the dogs.

Hence, the production of recombinant proteins is expensive, technically demanding, time consuming and very inefficient. In many cases, recombinant proteins may have useful effects but cannot be used because of the cost involved in their production. For example, numerous anti-tumor peptides are known to have beneficial effects, including apparent reduction or curing of cancers (for example, angiogenesis blockers). It has been recently claimed that angiostatin and endostatin can cure cancers in mice. However, the cost of producing these peptides (which may run as high as $5–20 million for the quantity of agent necessary for a single treatment regimen) prevents their use in cancer therapy. Thus, a cost-effective method of producing recombinant peptides or proteins that maintains their function (enzymic, antigenic, or other functional properties) is desperately needed.

Many constitutively produced proteins and peptides have closely associated "helper proteins" which help induce or maintain proper shape. These helper proteins are often call "chaperones" because they accompany the proteins through the production process. Some of these chaperone proteins bind to other proteins to prevent denaturation (loss of conformation) or other deterioration due to environmental stress. For example, the heat shock proteins (such as hsp70 and hsp90) are produced by cells in response to higher than normal levels of heat. Such heat shock proteins bind to other proteins within a cell, stabilizing them and thereby helping to maintain correct conformation and function of the bound protein. These and other, similar proteins that are produced in response to other stresses are in general called stress proteins.

The structure and functional role of such stress proteins appears to be highly conserved throughout nature, where the various stress proteins appear to play similar chaperone roles in both procaryotic and eucaryotic cells. This has lead to a large number of studies of and proposed uses for such proteins. For example, a number of works in the literature describe uses for such proteins based on in vitro contact of various biological materials with exogenously-produced stress proteins. These works, which are summarized below, are incorporated herein by reference:

Neupert et al. (U.S. Pat. No. 5,302,518) suggest that proper folding of proteins may be mediated in vivo by constitutive heat shock proteins, such as GroEL and hsp60 (which occur in *E. coli* and in eucaryotic mitochondria, respectively, and which appear to be virtually identical in form and function). Neupert thus describes methods for post-production modification of the folding of recombinant proteins based on in vitro contact of such denatured recombinant proteins with quantities of heat shock proteins that have been isolated from cells.

Berberian et al. (U.S. Pat. No. 5,348,945) describe methods for enhancement of cell survival under stressful conditions, such methods consisting of in vitro or in vivo application (i.e. addition) of exogenously produced, purified heat shock proteins, such as hsp70, to such stressed cells.

Jacob et al. (U.S. Pat. No. 5,474,892) suggest that certain proteins may be stabilized in aqueous solution via addition of quantities of certain heat shock proteins (such as hsp90). Jacob et al. thus describes post-production methods for modification of the folding or other stabilization of various proteins and other biological materials through in vitro contact of such denatured proteins with quantities of isolated and purified heat shock proteins.

Srivastava (U.S. Pat. Nos. 5,750,119; 5,830,464; and 5,837,251) suggests that tumor proliferation in mammals may be inhibited through inoculation of such mammals with antigenic compounds resulting from association of certain tumor components with various constitutive or exogenous stress proteins. Srivastava therefore describes methods for isolation or formulation of such stress protein/tumor complexes using various tumor specimens, and the subsequent inoculation of mammalian patients with such preparations for the purposes of stimulating anti-tumor response in such patients.

Liu et al. (J. Biol. Chem. 13 (1998) 30704) describe studies of the role of several heat shock proteins, such as hsp40 and hsp70, in enhancement of protein function. In vitro addition of purified exogenously produced heat shock proteins to denatured proteins was reported to lead to enhanced protein function. A co-chaperone role of hsp40 with hsp70 was also noted.

Other pertinent references concerning stress protein function, which are herein incorporated by reference, include:

McGuire et al. (U.S. Pat. Nos. 5,188,964 and 5,447,843) describe measurement of the levels of various constitutively produced stress proteins (including the heat shock proteins hsp27, hsp70, and hsp90, and the glucose regulated proteins grp 78 and grp94) present in tumor tissues and use of such measurements as a means for predicting probability of recurrence of such tumors.

Williams et al. (J. Clin. Invest. 92 (1993) 503) describe means for possible protection of cells and tissues from various metabolic stresses, such as ischemia, through transfection with the hsp70 gene. Specifically, constitutively expressed human hsp70 introduced into murine cells enhanced survival of such modified cells upon application of metabolic stress. Addition of such constitutive genes did, however, appear to negatively affect cell proliferation due to the metabolic burden of continual expression, even under unstressed conditions.

Vasconcelos et al. (J. Gen. Virol. 79 (1998) 1769) describe means for induction of enhanced expression of constitutive stress protein prior to infection of permissive Vero cell lines with HMV, leading to transient formation of large plaque phenotype variants of HMV. Cells infected 12 hours post stress (where such interval was chosen to allow cells to recover normal physiologic capacity while assuming that induced heat shock protein levels would be maintained over such interval) were found to exhibit slightly enhanced HMV production levels (characterized by up to four-fold increase in viral titer).

Vasconcelos et al. (J. Gen. Virol. 79 (1998) 2239) describe further means for transient enhancement of stress protein expression through transfection of permissive cell lines (such as human astrocytoma cells) with vectors coding for constitutive hsp72 expression. Clonal cell lines exhibiting uptake of the hsp72 gene were shown to yield increased viral titer upon infection with HMV. However, such clonal cell lines did not exhibit permanent modification, but rather exhibited a marked tendency to spontaneously regress to the wild-type form. Further, no means for control of expression of the constitutive hsp72 gene is proposed, leading to continuous expression by the modified cell lines. Applicability of the clonal cells produced in this work was limited to HMV—attempts to produce other viral products, for example CDV, were unsuccessful. Taken in conjunction with the transient nature of the modification, this suggests limited applicability of this approach.

Yokoyama et. al. (U.S. Pat. No. 5,827,712) describes methods for enhancement of yield in recombinant production of transglutaminase (TG) in *E. coli* modified for (via transfection) or selected for constitutive overexpression of certain chaperone proteins, including DnaJ and DnaK. Such overexpression is used to stabilize and solubilize functional recombinant TG. Methods for modification include incubation of stress protein vector and TG vector with *E. coli*. Incubation of a combined stress protein vector/TG vector with *E. coli*, and incubation of TG vector with *E. coli* strains exhibiting constitutive overexpression of stress protein. Notably, such methods are likely to yield transient modification wherein such stress protein is continuously produced, negatively affecting cell proliferation due to the metabolic burden of continual stress protein expression.

These examples of prior art clearly establish the role and utility of various stress proteins, such as hsp27, hsp40, hsp60, hsp70 (including hsp72 and hsp73), hsp90, GroEL, GroES, GrpE, grp 78, grp94, DnaJ and DnaK, as aids to enhanced production and stabilization of functional biological materials (such as proteins, viral agents, or other biological agents or products, including enzymes, hormones, growth factors, structural proteins and tumor suppressor agents). However, the methods and concepts taught in these examples, including methods for addition of exogenously produced stress proteins and for induction of transient constitutive production of such proteins, are not sufficiently efficient nor flexible for enhancement of yield in routine production of various biological agents or products, nor for discovery of new biological agents or products. For example, manufacture and purification of useful quantities of stress protein for addition to or modification of product will generally be prohibitively time consuming and expensive. Furthermore, transfection of cells with stress protein vectors coding for constitutively produced stress proteins will, unless incorporating suitable control elements, lead to full-time production of such stress proteins by such cells that will compete with production of desired biological products by such cells. Hence, new, more efficient ways for harnessing and controlling the capabilities and use of such stress proteins are required.

SUMMARY OF THE INVENTION

The present invention is directed to new and more efficient methods for harnessing and controlling the capabilities and use of stress proteins in the production and stabilization of functional biological materials, such as proteins, viral agents, or other biological agents or products, including, but not limited to, enzymes, hormones, growth factors, structural proteins, tumor suppressor agents, nucleic acids and nucleic acid probes, vaccines, antigens, antibiotics, lipids, simple and complex carbohydrates, alcohols and other solvents and the products of those methods. Examples of pertinent stress proteins of the present invention include, but are not limited to, hsp27, hsp40, hsp60, hsp70 (including hsp72 and hsp73), hsp90, GroEL, GroES, GrpE, grp 78, grp94, DnaJ and DnaK. In one embodiment of the present invention, the present invention causes the cells to make such hsp's, as opposed to adding them to the cells.

Specific preferred embodiments of the present invention include, either through the selective induction of constitutive expression of such stress proteins in or through transient or permanent introduction of such stress protein genes into, procaryotic or eucaryotic cells or cell lines, methods for making various non-permissive cell lines permissive, for increasing yield of various biological products, and for discovery and production of various unknown infectious agents.

For example, the use of such embodiments with such cells or cell lines causes dramatic increase in yield of recombinant products in procaryotic or eucaryotic cell lines. This is surprising, since intuitively, one would expect that increasing cellular stress during production would result in decreased productivity. The inventors of the present invention have found, however, that by stressing such cells by certain specific methods or otherwise inducing cellular stress response, thereby leading to controlled expression of stress protein genes, production of functional biological products can be enhanced.

The present invention is directed to such methods and includes the five preferred embodiments specifically illustrated herein. The present invention, however, is not limited to the specifics of these five embodiments but includes modifications and substitutions within the spirit and scope of the invention, as well as other embodiments which will become apparent to those skilled in the art upon reference to this description.

In the first preferred embodiment, transient stress of a eucaryotic cell line is used to enhance viral titer. Permissive eucaryotic cells are transiently stressed for a period sufficient to stimulate production of one or more stress proteins. A desired virus stock is subsequently added following application of this stress so as to infect the stressed eucaryotic cells. Following a period of post-infection incubation, the resulting supernatant, containing the desired virus-induced product, is then harvested.

In the second preferred embodiment, transient genetic modification of a eucaryotic cell line through episomal insertion of a stress protein expression vector, followed by selection of one or more subsets of these modified cell lines that exhibits permanent insertion of the expression vector into host DNA, is used to produce cell lines exhibiting permanent genetic modification. Such cell lines may be used to enhance production of a desired virus or viral product.

In the third preferred embodiment, production of a new permissive eucaryotic cell line is effected through insertion of a stress protein expression vector into a non-permissive eucaryotic cell line. The new permissive cell line is then used to efficiently produce viral agents through inoculation of the cell line with infective or potentially infective material, followed by incubation and harvest of the resultant virus or viral products thereby produced. Such cell lines are preferentially used to facilitate replication of difficult to grow neural agents and those never cultured before. Hence, such lines may be used both as virus hunters and for production or manufacture of useful quantities of agent.

In the fourth preferred embodiment, production of functional recombinant product by genetically engineered procaryotic cell lines is enhanced through insertion of one or more stress protein expression vectors into such cell lines. It is preferred that recombinant cells be selected for use. However, clonal cells may also be selected. It is further preferred that such inserted stress protein expression vectors include one or more inducible promoter. Alternatively, a constitutive promoter can be used. Expression of such stress protein expression vectors, either by induction or by constitutive expression, in such cell lines results in production of the one or more coded stress protein, wherein such expressed stress protein thereby serves to assist in enhancement of yield of functional recombinant product.

In the fifth preferred embodiment, production of functional recombinant product using genetically engineered eucaryotic cell lines is enhanced through insertion of one or more stress protein expression vectors into such cell lines. Such insertion may be effected prior to or after genetic modification of the line for production of the desired recombinant product. It is preferred that such stress protein expression vectors include one or more inducible promoter. Alternatively, a constitutive promoter can be used.

BRIEF DESCRIPTION OF THE DRAWINGS

In describing the preferred embodiments, reference is made to the accompanying drawings wherein:

FIG. 4a is an illustration of a method for the enhancement of recombinant product yield in genetically engineered procaryotic cell lines, in accordance with the present invention; and FIG. 4b is an illustration of an alternate method for the enhancement of recombinant product yield in genetically engineered procaryotic cell lines, in accordance with the present invention.

DETAILED DESCRIPTION OF THE PRESENTLY PREFERRED EMBODIMENTS

The present invention is directed to methods for enhancing production of a viral agent, production of cell lines exhibiting permanent genetic modification, production of permissive eucaryotic cell lines, enhancing functional recombinant product yield, and the products of such methods, as shown in the following embodiments and examples which are not intended to limit but merely illustrate the present invention.

First Preferred Embodiment

Figure 1:
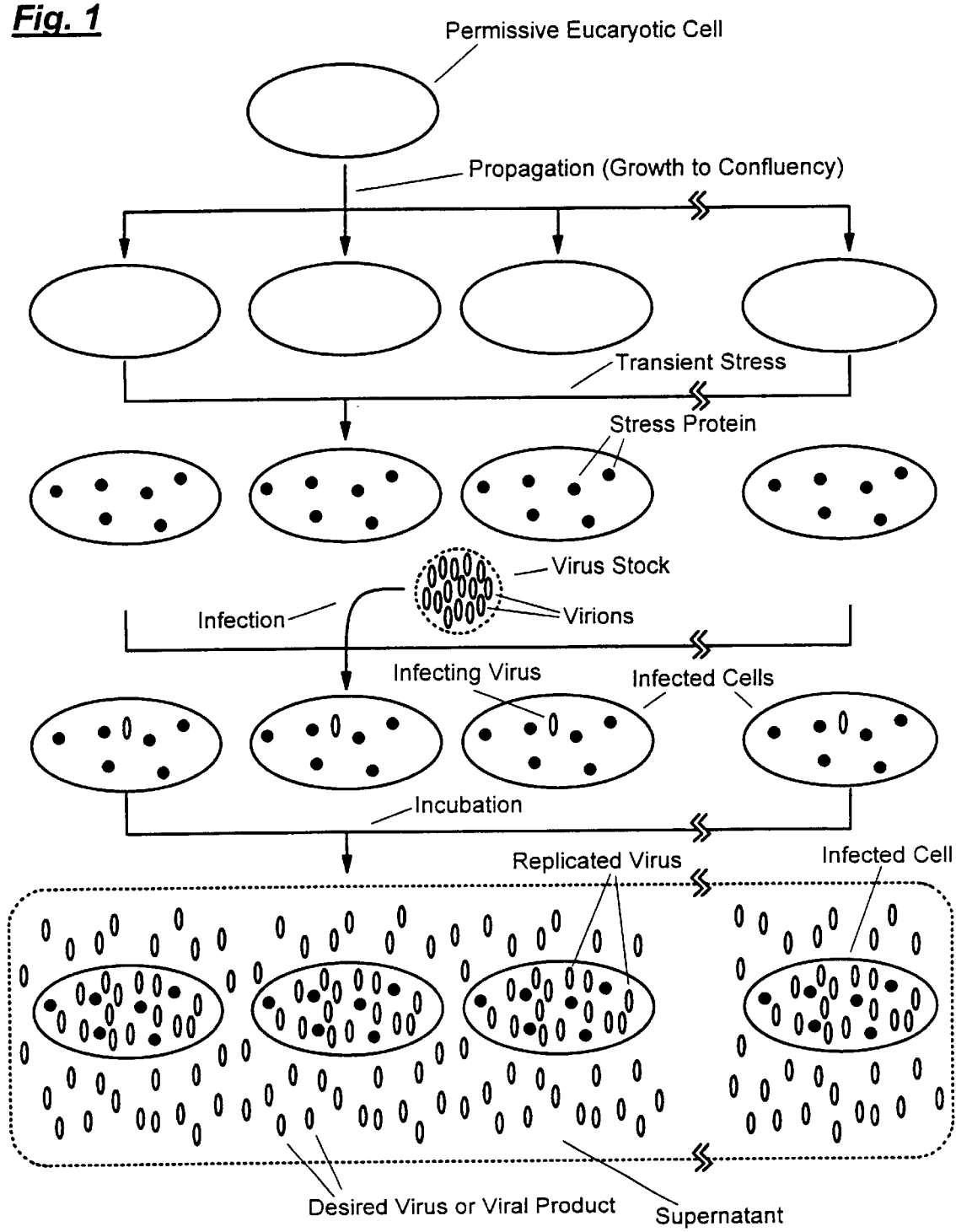
FIG. 1 is an illustration of the use of transient stress of permissive eucaryotic cell lines for enhancement of viral titer, in accordance with the present invention.

Permissive eucaryotic cells used for production of a desired virus or viral product may often be inadequately productive. The inventors of the present invention, however, have discovered that productivity of these cell lines may be transiently enhanced through application of a transient stress, as shown in FIG. 1 and illustrated in this embodiment.

In general, in this embodiment, transient stress of a eucaryotic cell line is used to enhance viral titer. More specifically, permissive eucaryotic cells for the desired virus are selected using conventional selection methods. Such cells are grown to an approximate confluency under standard conditions, and are then transiently stressed for a period sufficient to stimulate production of one or more stress protein. Applicable stress factors include thermal stress (such as increased or reduced incubation temperature), chemical stress (such as increased or reduced pH), oxidation level stress (such as increased or reduced levels of $O_2$), nutrient modification (such as reduction or enhancement of essential culture media components), and any other such factors (such as exposure to toxic substances) that can induce transient stress and resultant stress protein expression. A desired virus stock is subsequently added following application of this stress so as to infect the stressed eucaryotic cells. It is preferred that this addition be performed at a multiplicity of infection of 0.001–1000 virions per cell, or more preferably at 1–4 virions per cell, and that such addition be performed at a period of 0–12 hours post stress, or more preferably, immediately post stress. The resulting supernatant, containing the desired virus-induced product, is then harvested following a period of post-infection incubation. It is preferred that such harvest be performed after 1–2 or more days of post-infection incubation, or more preferably, 5 days post-infection.

EXAMPLE 1

Transient Stress of Eucaryotic Cell Lines for Enhancement of Viral Titer

Example 1 illustrates an example of the first embodiment. The present invention and the first embodiment, however, are not limited to the specifics of Example 1.

Permissive eucaryotic cells (such as Vero cells or other permissive eucaryotic cell lines) for the desired virus (such as Canine Distemper, Mink Distemper, or Human Measles Virus) are selected. Other viruses to which these cells are permissive include, but are not limited to, Rabies, Parvo, Marek's agent, HIV, HTLV, HSV, and Corona viruses. Such cells are grown to a confluency of approximately 90% or greater under standard conditions, such as at 37° C. with 5% $CO_2$. The cells are then transiently stressed for a period of up to several hours, for example by incubation at 43° C. with no $CO_2$ (thereby producing hyperthermic alkaline conditions in the culture). This transient stress is ideally applied for a period of approximately 1–5 hours. Enhanced production of various stress proteins, such as hsp70, is thereby induced in such cells. If these cells are subsequently infected with a virus, these increased stress protein levels will serve to stabilize and enhance production of virus-induced proteins by such stressed cells (see for example Table 3).

Optimal stress conditions can be determined for a particular cell/virus system based on two related factors: cell viability and viral titer. While cell viability (the fraction of cells surviving the stress period) is in general reduced by application of transient stress, the yield of stress protein (the relative quantity of protein produced, on average, by a cell) is in general increased by application of such stress. Hence, optimal stress conditions exist when cell viability exhibits minimal reduction but stress protein yield exhibits significantly enhanced expression of protein. Beyond this point, decreased viability can negatively affect overall yield, since significant loss of productive cell numbers can decrease overall protein production capacity of a culture. For example, TABLE 1 compares viability of Vero cells under various stress conditions. TABLE 2 compares protein yield from CDV-infected Vero cells under example stress conditions.

In Table 1 below, the viability of Vero cell cultures was estimated using neutral red staining, followed by measurement of the absorbance (at 570 nm) of resulting samples. Relative viability (non-normalized) is expressed in absorbance units, which corresponds to approximate level of viable cells following application of transient stress. Test conditions consisted of exposure of cell cultures to indicated temperatures under alkaline conditions (no $CO_2$) for the specified duration.

TABLE 1

Effects of transient stress severity and duration on cell viability

| Test Conditions | | Relative Viability |
|---|---|---|
| Temperature | Duration | $A_{570\ nm}$ |
| 37° C. | 1.5 hour | 0.25 ± 0.03 |
| 37° C. | 3 hour | 0.23 ± 0.03 |
| 37° C. | 5 hour | 0.21 ± 0.03 |
| 40° C. | 1.5 hour | 0.25 ± 0.10 |
| 40° C. | 3 hour | 0.22 ± 0.03 |
| 40° C. | 5 hour | 0.19 ± 0.09 |
| 43° C. | 1.5 hour | 0.21 ± 0.03 |
| 43° C. | 3 hour | 0.18 ± 0.03 |
| 43° C. | 5 hour | 0.13 ± 0.03 |

In Table 2 below, the indicated stress conditions were applied to Vero cell cultures for a duration of 2 hours, followed by immediate CDV infection. Infected cell cultures were then incubated under standard conditions (37° C. with 5% $CO_2$) following this transient stress period. Titer was determined by serial dilution (10×dilution per step) of harvested supernatant into 96-well plates containing fresh confluent Vero cultures. These infected samples were then incubated for 4 days, followed by fixation with neutral buffered formalin. Resultant fixed wells were then stained with fluorescein-conjugated anti-CDV antibodies and read by cytofluorimetry. Titer results represent number of dilution steps resulting in positive viral infection.

TABLE 2

Effect of transient stress on virus product yield.

| Test Conditions | $\log_{10}$(Viral Titer) |
|---|---|
| 37° C. + Alkalinity (pH = 7.6) | 3 |
| 40° C. + Alkalinity (pH = 7.6) | 5 |
| 43° C. + Alkalinity (pH = 7.6) | 8 |

Comparison of the example results shown in TABLES 1 and 2 indicate that viral titer in Vero cells is increased significantly at 43° C. relative to less stressful culture conditions, and that exposures of 3 hours or less under such conditions do not significantly impair viability of the test cultures. Hence, for this cell/virus combination, optimal conditions are approximated by stressing cultures at 43° C., 0% $CO_2$, for two hours immediately prior to viral infection. Further, refinement of these conditions is possible through more detailed evaluation of various stress conditions, not specifically limited to those conditions or ranges described here. Moreover, for other cell/virus combinations, other parameters will likely be optimal. However, these examples clearly demonstrate the general approach used for such optimization. Using such an approach, a skilled practitioner can readily determine the optimal conditions for a specific cell/virus combination.

Optimally, the desired virus stock (e.g., CDV) is added to the cells immediately after the stress period, but such cells may be infected up to 24 or more hours post stress. Virus stock is added at a multiplicity of infection (MOI) of 0.001–1000 virions per cell, or more preferably at 1–4 virions per cell, the latter levels being more optimal. MOI may vary depending on the cell line and virus being produced. Following a final incubation period, supernatant is optimally harvested several days post infection. For Vero cells infected with CDV, such harvest is optimally performed at 5 days post infection, but under some conditions 1–21 or more days may be required. Optimal conditions may be determined by measurement of viral titer as a function of harvest time. Viral titers thereby produced will be increased 10–100 times or more, as shown in TABLE 3 (for example, from the initial titer of approximately $10^5$ to an enhanced titer of $10^{7-8}$). In TABLE 3 below, Vero cell cultures were stressed for two hours prior to CDV infection by elevation of temperature to 43° C. under alkaline conditions (no $CO_2$). Infected cultures were maintained at 37° C. with 5% $CO_2$ following this transient stress period. Control conditions: unstressed cultures maintained at 37° C. with 5% $CO_2$. Titer results were obtained in the manner indicated above in TABLE 2.

TABLE 3

CDV titer produced by transient stress

| Infection Conditions | $\log_{10}$(Viral Titer) |
| --- | --- |
| Control (unstressed) | 4.7 |
| 0 hour post stress | 8.5 |
| 2 hour post stress | 7 |
| 6 hour post stress | 7 |
| 12 hour post stress | 5 |

Second Preferred Embodiment

Figure 2:
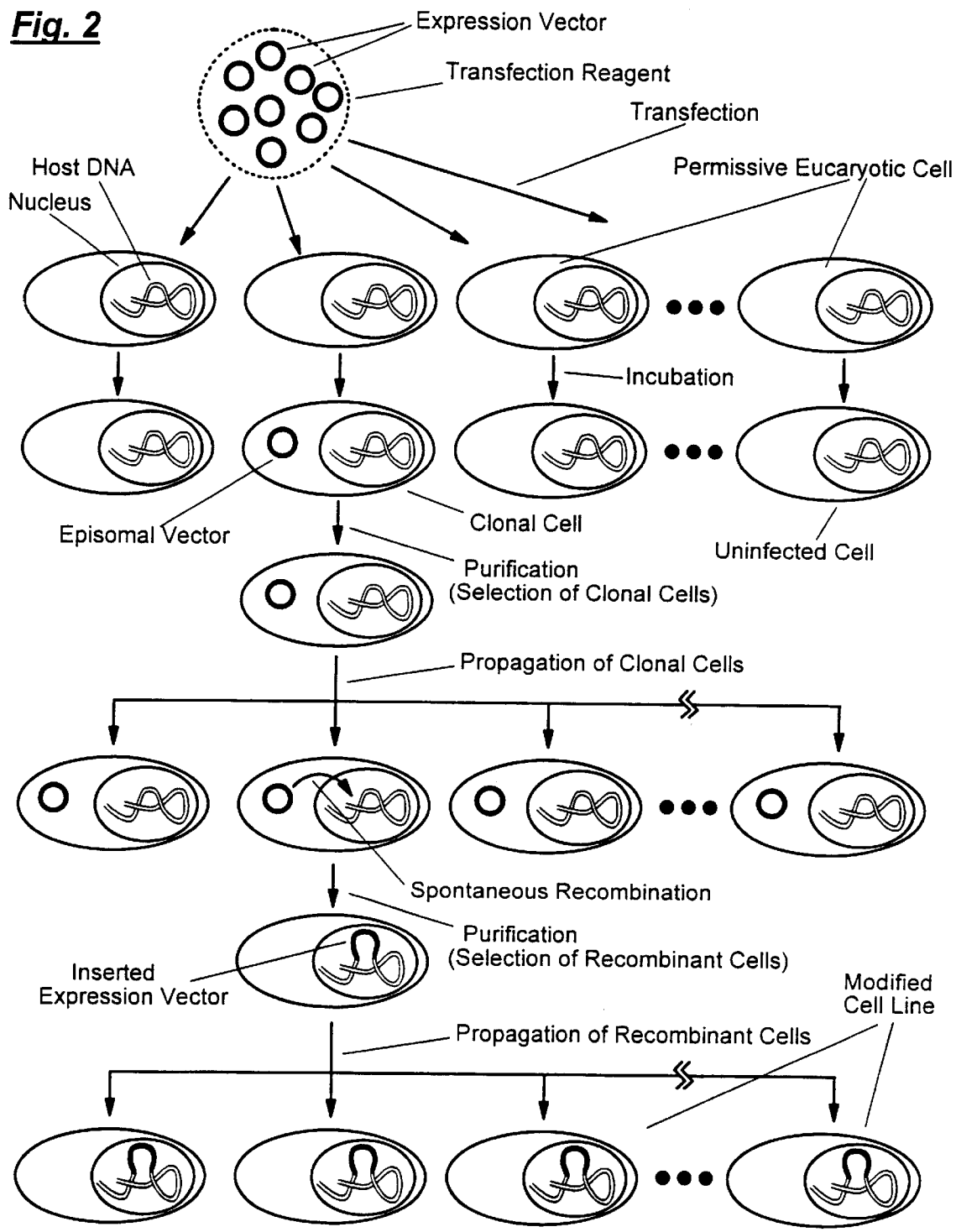
FIG. 2 is an illustration of the permanent genetic modification of a permissive eucaryotic cell line via transient genetic modification, in accordance with the present invention.

Often, permissive eucaryotic cells (such as Vero cells or other permissive eucaryotic cell lines) used for production of a desired virus or viral product are inadequately productive. The inventors of the present invention, however, have discovered that these cells may be genetically modified so as to enhance yield upon infection with the desired virus, as shown in FIG. 2 and illustrated in this embodiment.

In this embodiment, transient genetic modification of a eucaryotic cell line through episomal insertion of a stress protein expression vector, followed by selection of one or more subsets of the modified cell lines (resulting from the insertion of the stress protein expression vector) that exhibit permanent insertion of the expression vector into host DNA, is used to produce cell lines exhibiting permanent genetic modification, as shown in FIG. 2. Such cell lines may be used to enhance production of a desired virus or viral product.

More specifically, permissive eucaryotic cells for the desired virus are selected using conventional selection methods and are grown to an approximate confluency under standard conditions. A DNA transfection reagent for these eucaryotic cells is prepared by mixing a stress protein expression vector with a lipid/phospholipid preparation to yield a transfection reagent with a concentration of approximately 0.01–100 $\mu$g of vector per $10^4$–$10^6$ target cells. It is preferred that this lipid/phospholipid preparation include cationic lipids or phospholipids, and more preferably, that it contain dioleoylphosphatidalethanolamine. This transfection reagent is then delivered to the permissive cell culture, allowing transfection to occur. Following transfection, the culture is incubated in fresh culture media. To increase transfection yield, the transfection step may subsequently be repeated: The resultant genetically heterogeneous cell culture is then purified by selection of those cell lines exhibiting high-yield expression of the transfected stress protein and enhanced ability to propagate the desired virus. From this fraction, further purification is performed by selection of those cell lines exhibiting spontaneous recombination of the expression vector into host DNA. Cell lines that exhibit such recombination are thus permanently genetically modified and are kept for recombinant protein or viral production.

EXAMPLE 2

Permanent Genetic Modification of a Permissive Eucaryotic Cell Line Via Transient Genetic Modification Example 2 illustrates an example of the second embodiment. The present invention and the second embodiment, however, are not limited to the specifics of Example 2.

Permissive eucaryotic cells for the desired virus are selected and grown to a confluency of approximately 90% or greater under standard conditions, such as at 37° C. with 5% $CO_2$.

A DNA transfection reagent for these eucaryotic cells is prepared by mixing a stress protein expression vector (such as for example, a virus, cosmid, plasmid, phage, transposon, or any other transmissible vector, including DNA or RNA, that is capable of insertion into eucaryotic cellular DNA and thereby increasing the stress protein expression of the eucaryotic cells upon transfection of such cells) with a lipid/phospholipid preparation to yield a transfection reagent with a concentration of approximately 0.01–100 $\mu$g of vector per $10^4$–$10^6$ target cells. As explained above, it is preferred that this lipid/phospholipid preparation include cationic lipids or phospholipids, and more preferably, that it contain dioleoylphosphatidalethanolamine. However any other compatible phospholipid may be used in conjunction with one or more cationic lipid. This transfection reagent is then diluted in serum-free culture medium and incubated on the permissive eucaryotic cells for 10–60 minutes or longer, allowing transfection to occur. Supernatant is then removed from the cell culture, and fresh culture medium, such as for example fetal bovine serum at a concentration of approximately 10% v/v, is added. This culture is then incubated for several or more hours, such as overnight. Finally, to further increase transfection yield, this lipofection procedure may be repeated 24–48 hours later. Lipofection is the optimal method for introducing the stress protein expression vector (for example, for expression of hsp70, hsp90, or other stress or chaperone proteins), but other standard techniques like electroporation may also be used. Genetic modification using a viral insertion vector may also be used.

The transfection process described above produces a genetically heterogeneous cell culture in which a fraction of the cells have undergone transient genetic modification (consisting of episomal insertion of the stress protein expression vector into the cell without significant spontaneous recombination of this vector into host cell genetic material). Such a culture will exhibit a transient genetic modification (characterized by expression of the episomal vector) but will generally not include a significant portion of cells exhibiting permanent modification. Since the episomal vector is not incorporated into host cell genetic material, such cultures can spontaneously revert to the uninfected form through expulsion of this episomal genetic material.

Hence, to obtain a stable culture exhibiting permanent modification, a subset of these cells must thus be selected and propagated. For example, transfected cells may exhibit a transient, high-yield expression of stress protein (such as hsp70) due to transient genetic modification. If the transfected cell cultures are trypsinized, the released cells can be serially diluted to extinction, for example in a 96 well culture plate. Cell cultures that arise in wells near the extinction point are considered to be clonal and are harvested. These genetically modified cell lines are then tested for the ability to grow increased levels of virus (for example, as described in Example 1) and measured for enhanced expression of stress protein (for example using standard enzyme-linked immunosorbant assay (ELISA) for expression levels of the particular stress protein, such as hsp70). Cell lines passing these tesis are then probed (using standard assays such as gel electrophoresis followed by Southern blot assay of the separated nucleic acids) for insertion of the expression vector into host DNA via spontaneous recombinational events. Note that such insertion occurs spontaneously at a rate of approximately 1 recombinational event in $1\times10^3$ cell divisions. However, recombinational efficiency may be much lower depending on specific vector and cell lines used and may therefore necessitate additional selection steps. Recombinant cell lines that exhibit a stable insertion into the host cell's genetic material, and are thus permanently genetically modified, are kept for recombinant protein or viral production lines. Such cell lines will exhibit desirable improvements in yield of a desired virus or viral product as a result of the incorporation of the stress protein gene and commensurate enhancement of stress protein production.

Third Preferred Embodiment

Often, permissive eucaryotic cells necessary for production of a desired agent, such as a virus or viral product, are non-existent or inadequately productive. For example, culturing of agents that affect the central nervous system can be very difficult since few cells are permissive to such agents. Specifically, agents such as the Creutzfeld-Jacob agent, scrapie, Kuru, Rabies, and Bovine Spongiform Encephalopy (nvCJD) are difficult or impossible to culture in vitro because of a lack of adequate permissive cell lines. Hence, there is a need for new process for production of permissive cell lines for such agents.

In this embodiment, non-permissive eucaryotic cells are genetically modified so as to be made permissive, and production of a new permissive eucaryotic cell line is effected through insertion of a stress protein expression vector into a non-permissive eucaryotic cell line. The news permissive cell line is then used to efficiently produce viral agents through inoculation of the cell line with infective or potentially infective material, followed by incubation and harvest of the resultant virus or viral products thereby produced. Such cell lines are preferentially used to facilitate replication of difficult to grow neural agents and those never cultured before. Hence, such lines may be used both as virus hunters and for production or the manufacture of useful quantities of agent.

EXAMPLE 3

Production of New Permissive Cell Lines

Example 3 illustrates an example of the third embodiment. The present invention and the third embodiment, however, are not limited to the specifics of Example 3.

Figure 3:
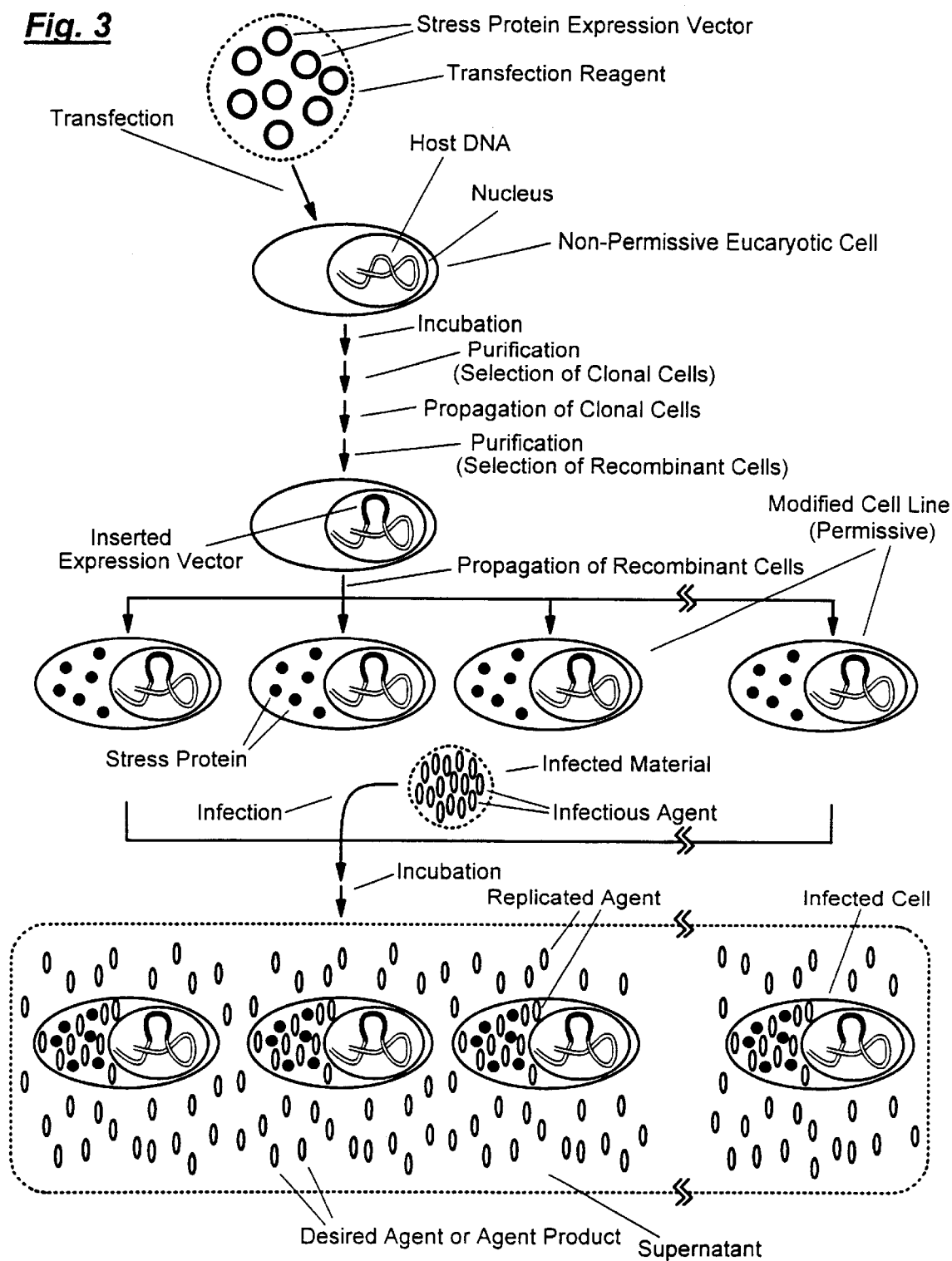
FIG. 3 is an illustration of a method for the production of new permissive eucaryotic cell lines, in accordance with the present invention.

In this example, non-permissive eucaryotic cells, such as insect cells, are genetically modified so as to be made permissive for the desired virus, as shown in FIG. 3. Neural cell lines, such as neuroblastoma, astrocytoma, or retinoblastoma cell lines, can be transfected with a stress protein expression vector, as described in Example 2. This yields a new cell line capable of efficiently producing viral agents. It is preferred in this process that recombinant cell lines be selected for subsequent use. Alternatively, clonal cell lines may also be used. Infected or potentially infected material, such as animal offal, containing a known or suspected infectious agent, is then used to inoculate these genetically modified cell lines. Such cell lines will facilitate replication of difficult to grow neural agents like rabies and those never cultured before (for example, nvCJD), and may be used both as a virus hunter (used to produce characterizable quantities of a suspect infectious agent) and for manufacture of large quantities of agent (for example, in the production of a new vaccine). Examples of new permissive cell lines produced from non-permissive cell lines are shown in TABLE 4.

In Table 4 below, there is shown the results of a comparison of human measles virus (HMV) titer raised in native (untreated), non-permissive cell lines (Line A, neuroblastoma; Line B. retinoblastoma) and in the same cell lines following treatment to insert hsp70 stress protein expression vector. Increased titer following treatment is indicative of markedly enhanced permissiveness of these cells to HMV. Enhancement of titer in multiple cell lines is indicative of the general applicability of this method to various candidate cell lines and infectious agents.

TABLE 4

Effects of inserted stress protein expression vector on viral titer

| Cell Line | Treated | $\log_{10}$(Viral Titer) |
|---|---|---|
| A | No | 1.10 |
| A | Yes | 6.70 |
| B | No | 1.60 |
| B | Yes | 6.30 |

Fourth Preferred Embodiment

Procaryotic cell lines are frequently used for production of proteins or other biological materials via recombinant methods, i.e. genetic material coding for the production of a desired product is introduced into the cell line, resulting in the production of the desired product by the procaryotic cells. For example, human insulin may be produced using bacteria that have been genetically engineered through the introduction of the necessary human genes coding for production of the desired insulin proteins. Unfortunately, such recombinant products often fail to exhibit the same biological function as the constitutively produced materials (i.e., materials produced via natural means). This frequently is the result of incomplete or improper folding (or changes in other similar factors affecting conformation) during the recombinant production process. Such changes in folding or conformation often result in a denatured protein, negatively affecting proper function of the product. Hence, a process for enhancing yield of functional recombinant product is needed.

In this embodiment, production of functional recombinant product by genetically engineered procaryotic cell lines is enhanced through insertion of one or more stress protein expression vectors into such cell lines. It is preferred that recombinant cells be selected for subsequent use. Alternatively, clonal cells may also be selected. It is further preferred that such inserted stress protein expression vectors include one or more inducible promoter. Alternatively, a constitutive promoter can be used. Expression of such stress protein expression vectors, either by induction or by constitutive means, in such cell lines results in production of the one or more coded stress protein, wherein such expressed stress protein thereby serves to assist in enhancement of yield of functional recombinant product. Such enhancement is optimally achieved through insertion and subsequent induction of suitable stress protein expression vectors, such as hsp70 or hsp90, but any other stress protein expression vector is applicable. Such insertion is optimally achieved through transfection. However, electroporation or other similar techniques, along with cell line infection via exposure to one or more viral insertion vectors, may be used. Such enhancement methods may be used to enhance yield of functional product from a previously modified cell line, such as, for example one that has been modified to produce human insulin. Alternatively, a procaryotic cell already exhibiting a stable insertion that results in or promotes production of one or more stress proteins may be modified to produce viruses or other recombinant products (such as proteins, enzymes, insulin, or other desired biological products).

EXAMPLE 4

Enhancement of Recombinant Product Yield in Procaryotic Cell Lines

Example 4 illustrates an example of the fourth embodiment. The present invention and the fourth embodiment, however, are not limited to the specifics of Example 4.

As illustrated in this embodiment and examples, the inventors of the present invention have discovered an approach for enhancing functional recombinant yield that includes induction of one or more stress proteins in the procaryotic cell line, wherein such induced stress proteins serve to assist proper folding or other conformational changes of the recombinant product, thereby resulting in enhanced yield of functional recombinant product. This induction can be optimally achieved by insertion of a suitable stress protein expression vector (for example hsp70 or hsp90) into the recombinant procaryotic cell line, such as genetically engineered *Escherichia coli*. This insertion is optimally achieved using transfection. Alternatively, electroporation or other similar techniques may be used. This general process is illustrated in FIGS. 4a and 4b. Note that various viral insertion vectors may also be used to insert desired genetic elements coding for or promoting stress protein production. Insertion of the stress protein expression vector can result in recombinant insertion of the stress protein expression vector into the host genetic material, as illustrated in FIG. 4a, or episomal insertion, as illustrated in FIG. 4b. The resultant transfected cells are then screened using standard procedures to select those exhibiting high levels of stress protein expression. Using methods comparable to those used with eucaryotic cell lines, such as those described in Example 2, recombinant cell lines are selected that have a stable insertion into the host genetic material, as shown in FIG. 4a. Alternately, clones exhibiting episomal insertion may be used, as shown in FIG. 4b. The stress protein expression vector may in this manner be inserted into a previously modified cell line, such as, for example one that has been modified to produce human insulin. Alternatively, a procaryotic cell already exhibiting a stable insertion that results in or promotes production of one or more stress proteins may be modified to produce viruses or other recombinant products (such as proteins, enzymes, insulin, or other desired biological products).

It is preferable in the examples illustrated in FIGS. 4a and 4b that the stress protein expression vector include one or more inducible promoter. Alternatively, a constitutive promoter can be used. Inducible promoters are more desirable since they allow cell lines to be propagated to high levels without exhibiting significant expression of the inserted stress protein expression vector (such expression would tend to compete with expression of the desired recombinant product). Once such cell lines have reached the desired level of recombinant product production, induction of the inducible stress protein expression vector can be used to redirect production of the cell lines to stress protein, thereby assuring optimum efficiency in recombinant product production levels and yield of functional product. Examples of inducible promoters include, but are not limited to, β-galactosidase, retroviral steroid-sensitive, and heavy metal inducible promoters. If, in contrast, a constitutive promoter is used, cell lines may tend to devote a significant portion of production capacity on continuous or nearly continuous production of stress protein. Such production will yield a high proportion of functional product but will tend to compete with optimum cell line propagation and total production level of the recombinant product.

Fifth Preferred Embodiment

Eucaryotic cell lines may be used for production of desired proteins or other biological materials or products via recombinant methods, i.e. genetic material coding for production of a desired product is introduced into the cell line, resulting in production of the desired product by the eucaryotic cells. For example, human angiogenesis blocking peptides can be produced using eucaryotic cell lines that have been genetically engineered through the introduction of the necessary human genes coding for production of the desired products. Unfortunately, such recombinant methods often fail to yield the desired products with acceptable yield or in acceptable quantity. Further, such products may fail to exhibit the same biological function as the constitutively produced materials. Hence, a method for enhancing production level or yield of functional recombinant product is needed.

In this embodiment, production of functional recombinant product using genetically engineered eucaryotic cell lines is enhanced through insertion of one or more stress protein expression vectors into such cell lines. Such insertion may be effected prior to or after genetic modification of the line for production of the desired recombinant product. It is preferred that such stress protein expression vectors include one or more inducible promoter. Alternatively, a constitutive promoter can be used.

EXAMPLE 5

Enhancement of Recombinant Product Yield in Eucaryotic Cell Lines

Example 5 illustrates an example of the fifth embodiment. The present invention and the fifth embodiment, however, are not limited to the specifics of Example 5.

As illustrated in this embodiment and example, the inventors of the present invention have discovered an approach for enhancing yield of functional recombinant product that includes induction of one or more stress proteins in the eucaryotic cell line, wherein such induced stress proteins serve to assist proper folding or other conformational changes of the recombinant product, thereby resulting in enhanced yield of functional recombinant product. For example, an expression vector for production of a desired biological product (such as an angiogenesis blocking or enhancing peptide sequence) may be inserted into a eucaryotic cell line (such as a mammalian, insect or other cell line, and more preferably S-9 insect cell lines) before or after genetic modification of the line with a stress protein expression vector coding for production of a stress protein. Such modification with a stress protein expression vector (such as hsp70 or hsp90) is effected using methods described in Example 2. This stress protein expression vector may preferably include one or more inducible promoter. Alternatively, a constitutive promoter can be used. Stress protein thereby induced (as a result of such modification) facilitates enhanced production and stability of the desired recombinant product. Optimally, this procedure is used for the production of one or more peptides, but it may also be used to internally stabilize proteins required for the synthesis and assembly of a non-peptide product or other biological material, such as diagnostic nucleic acid probes, vaccines, antigens, enzymes, hormones, growth factors, structural proteins, tumor suppressor agents, antibiotics, lipids, nucleic acids, simple and complex carbohydrates, alcohols and other solvents.

This description has been offered for illustrative purposes only and is not intended to limit the invention of this application.

What is claimed as new and desired to be protected by Letters Patent is set forth in the appended claims.

We claim:

1. A method for the production of a viral entity selected from the group consisting of a virus, a viral antigen and a viral product, said method comprising the steps of:

inserting a DNA expression vector coding for a stress protein into a eucaryotic cell line that is non-permissive for said virus;

selecting from said eucaryotic cell line at least one modified eucaryotic cell line, wherein said at least one modified eucaryotic cell line is permissive for said virus;

introducing an infective material to said at least one modified eucaryotic cell line to produce at least one infected modified eucaryotic cell line;

incubating said at least one infected modified eucaryotic cell line; and harvesting at least one resultant viral entity from the group consisting of a virus, a viral antigen and a viral product from said at least one infected modified eucaryotic cell line.

2. The method of claim 1 wherein said production is for discovery of at least one unknown viral agent.

3. The method of claim 1 wherein said non-permissive eucaryotic cell line is selected from the group consisting of neuroblastoma, astrocytoma and retinoblastoma cell lines.

4. The method of claim 1 wherein said step of inserting is by transfection.

5. The method of claim 1 wherein said DNA expression vector is selected from the group consisting of hsp 70, hsp 72, hsp 73, hsp 90, GroEL, GroES, GrpE, grp 78, grp 94, DnaJ and Dnak.

6. The method of claim 1 wherein said at least one modified eucaryotic cell line is recombinant for said DNA expression vector.

7. The method of claim 1 wherein said at least one modified eucaryotic cell line is clonal for said DNA expression vector.

8. The method of claim 1 wherein said infective material is animal offal containing a suspected infectious agent.

* * * * *